United States Patent
Barbato et al.

(10) Patent No.: US 7,314,448 B2
(45) Date of Patent: *__Jan. 1, 2008__

(54) IMAGING TRANSDUCER ASSEMBLY

(75) Inventors: Louis J. Barbato, Franklin, MA (US); Isaac Ostrovsky, Wellesley, MA (US); Paul Goll, Danville, CA (US); Thomas C. Moore, Livermore, CA (US); Douglas M. Petty, Pleasanton, CA (US); Mark Hamm, Lynnfield, MA (US); Richard Romley, Tracy, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 265 days.

This patent is subject to a terminal disclaimer.

(21) Appl. No.: 10/754,292

(22) Filed: Jan. 9, 2004

(65) Prior Publication Data

US 2004/0193057 A1    Sep. 30, 2004

Related U.S. Application Data

(63) Continuation-in-part of application No. 10/401,901, filed on Mar. 28, 2003, now Pat. No. 7,081,094.

(51) Int. Cl.
*A61B 8/12* (2006.01)
(52) U.S. Cl. .................................. 600/466; 128/899
(58) Field of Classification Search ........ 600/459–471, 600/437; 128/899
See application file for complete search history.

(56) References Cited

U.S. PATENT DOCUMENTS

| | | | |
|---|---|---|---|
| 4,154,246 A * | 5/1979 | LeVeen ................... | 607/99 |
| 4,951,677 A * | 8/1990 | Crowley et al. .......... | 600/463 |
| 5,002,058 A | 3/1991 | Martinelli | |
| 5,054,492 A * | 10/1991 | Scribner et al. .......... | 600/463 |
| 5,115,814 A * | 5/1992 | Griffith et al. ........... | 600/463 |
| 5,176,140 A * | 1/1993 | Kami et al. ............... | 600/459 |
| 5,207,225 A | 5/1993 | Oaks et al. | |
| 5,228,176 A | 7/1993 | Bui et al. | |
| 5,243,988 A * | 9/1993 | Sieben et al. ............. | 600/463 |
| 5,259,837 A | 11/1993 | Van Wormer | |
| 5,351,693 A | 10/1994 | Taimisto et al. | |
| 5,353,798 A | 10/1994 | Sieben | |
| 5,368,035 A | 11/1994 | Hamm et al. | |
| 5,368,036 A | 11/1994 | Tanaka et al. | |
| 5,372,138 A * | 12/1994 | Crowley et al. .......... | 600/463 |
| 5,437,282 A * | 8/1995 | Koger et al. .............. | 600/463 |
| 5,488,954 A * | 2/1996 | Sleva et al. ............... | 600/459 |

(Continued)

FOREIGN PATENT DOCUMENTS

WO    WO92/03095    3/1992

*Primary Examiner*—Francis J. Jaworski
(74) *Attorney, Agent, or Firm*—Orrick Herrington & Sutcliffe LLP

(57) ABSTRACT

An improved medical imaging device assembly includes an imaging transducer coupled to the distal end of a drive shaft, and a conductive wire is wrapped around a distal portion of the drive shaft, wherein the conductive wire reinforces the imaging device assembly. In one embodiment, the conductive wire is part of a sensor adapted to communicate with a medical positioning system. In another embodiment, the conductive wire is configured to be a matching circuit for the imaging transducer. The conductive wire may be configured to be in parallel with the imaging transducer or configured to be in series with the imaging transducer.

26 Claims, 6 Drawing Sheets

U.S. PATENT DOCUMENTS

| | | | |
|---|---|---|---|
| 5,488,955 A * | 2/1996 | Dias | 600/459 |
| 5,515,853 A | 5/1996 | Smith et al. | |
| 5,546,947 A | 8/1996 | Yagami et al. | |
| 5,596,990 A | 1/1997 | Yock et al. | |
| 5,715,825 A | 2/1998 | Crowley | |
| 5,738,100 A | 4/1998 | Yagami et al. | |
| 5,846,205 A | 12/1998 | Curley et al. | |
| 5,938,602 A | 8/1999 | Lloyd | |
| 5,938,615 A | 8/1999 | Eberle et al. | |
| 5,951,480 A | 9/1999 | White et al. | |
| 5,954,649 A | 9/1999 | Chia et al. | |
| 6,019,725 A | 2/2000 | Vesely et al. | |
| 6,019,726 A * | 2/2000 | Webb | 600/459 |
| 6,095,976 A | 8/2000 | Nachtomy et al. | |
| 6,149,599 A | 11/2000 | Schlesinger et al. | |
| 6,161,032 A * | 12/2000 | Acker | 600/424 |
| 6,162,179 A * | 12/2000 | Moore | 600/466 |
| 6,165,127 A | 12/2000 | Crowley | |
| 6,245,020 B1 * | 6/2001 | Moore et al. | 600/466 |
| 6,248,075 B1 | 6/2001 | McGee et al. | |
| 6,259,941 B1 | 7/2001 | Chia et al. | |
| 6,283,920 B1 | 9/2001 | Eberle et al. | |
| 6,332,089 B1 * | 12/2001 | Acker et al. | 600/424 |
| 6,457,365 B1 | 10/2002 | Stephens et al. | |
| 6,461,298 B1 | 10/2002 | Fenster et al. | |
| 6,464,642 B1 | 10/2002 | Kawagishi | |
| 6,490,474 B1 | 12/2002 | Willis et al. | |
| 6,511,428 B1 | 1/2003 | Azuma et al. | |
| 6,520,916 B1 | 2/2003 | Brennen | |
| 6,592,520 B1 * | 7/2003 | Peszynski et al. | 600/437 |
| 6,593,884 B1 * | 7/2003 | Gilboa et al. | 342/448 |
| 6,607,488 B1 | 8/2003 | Jackson et al. | |
| 6,785,571 B2 * | 8/2004 | Glossop | 600/424 |
| 2002/0007120 A1 | 1/2002 | Moore et al. | |
| 2002/0026129 A1 | 2/2002 | White et al. | |
| 2002/0099289 A1 | 7/2002 | Crowley | |
| 2004/0133105 A1 * | 7/2004 | Ostrovsky et al. | 600/437 |
| 2004/0193041 A1 * | 9/2004 | Ostrovsky | 600/424 |
| 2005/0085716 A1 * | 4/2005 | Hamm et al. | 600/424 |
| 2006/0106314 A1 * | 5/2006 | Ostrovsky | 600/459 |

* cited by examiner

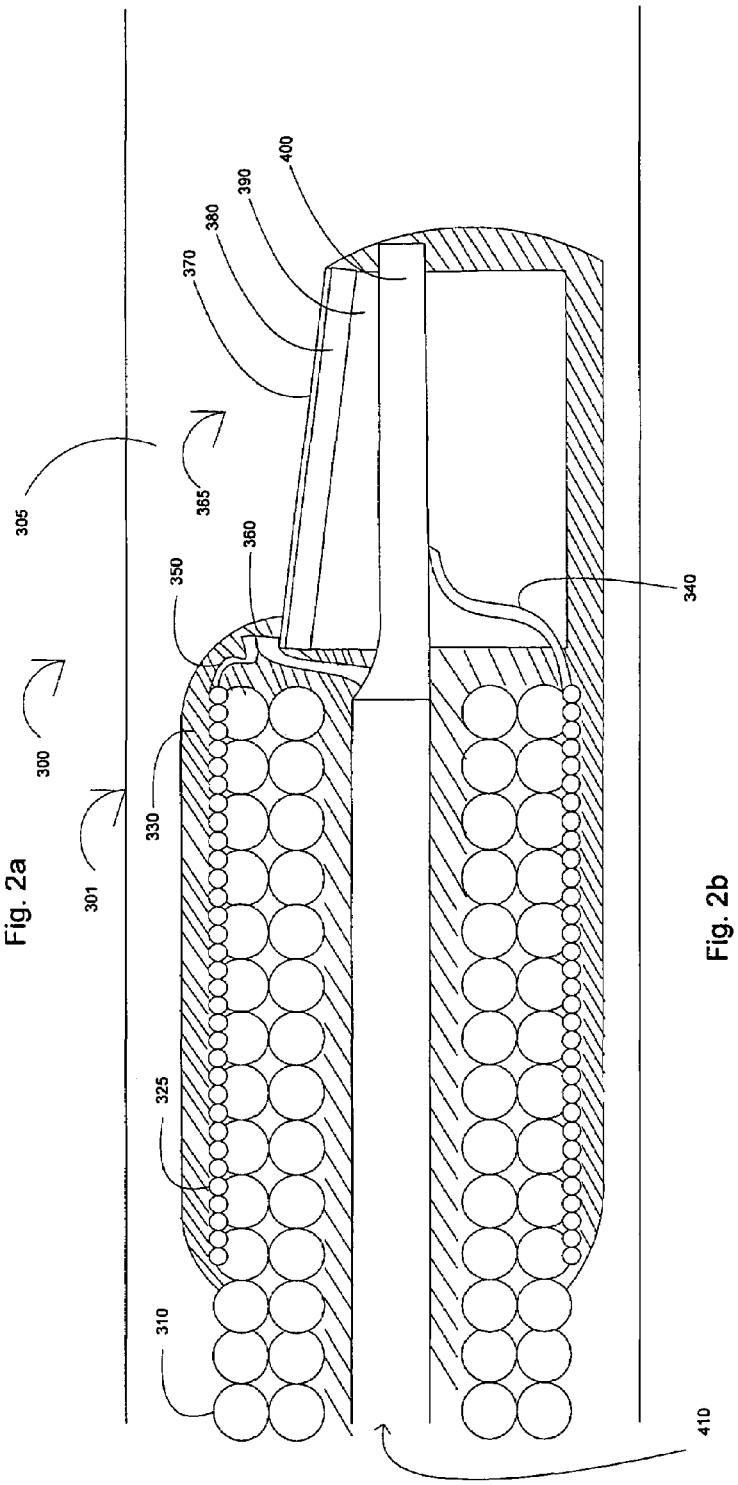

IMAGING TRANSDUCER ASSEMBLY

CROSS-REFERENCE TO RELATED PATENTS AND APPLICATIONS

This is a continuation-in-part of U.S. patent application Ser. No. 10/401,901, entitled "An Improved Imaging Transducer Assembly," filed on Mar. 28, 2003 now U.S. Pat. No. 7,081,094, which is hereby incorporated by reference in its entirety.

FIELD OF THE INVENTION

The field of the invention relates to medical imaging systems, and more particularly to an improved imaging transducer assembly.

BACKGROUND OF THE INVENTION

Intraluminal, intracavity, intravascular, and intracardiac treatments and diagnosis of medical conditions utilizing minimally invasive procedures are effective tools in many areas of medical practice. These procedures are typically performed using imaging and treatment catheters that are inserted percutaneously into the body and into an accessible vessel of the vascular system at a site remote from the vessel or organ to be diagnosed and/or treated, such as the femoral artery. The catheter is then advanced through the vessels of the vascular system to the region of the body to be treated. The catheter may be equipped with an imaging device, typically an ultrasound imaging device, which is used to locate and diagnose a diseased portion of the body, such as a stenosed region of an artery. For example, U.S. Pat. No. 5,368,035, issued to Hamm et al., the disclosure of which is incorporated herein by reference, describes a catheter having an intravascular ultrasound imaging transducer.

FIG. 1a shows an example of an imaging transducer assembly 1 known in the art. The imaging transducer 1 is typically within the lumen 60 of a guidewire (partially shown), having an outer tubular wall member 5. The imaging transducer assembly 1 includes a coaxial cable 110, having a center conductor wire 120 and an outer shield wire 140, shown in FIG. 1b. A conductive wire, having a diameter of approximately 500 microns, is wrapped around the coaxial cable 110, forming a coil, which functions as a drive shaft 10. Connected to the distal end of the drive shaft 10 is a stainless steel housing 20, which serves to reinforce the structure of the imaging transducer assembly 1. Surrounding the coaxial cable 110, within the housing 20 is a silver epoxy 30, a conductive material. Thus, the housing 20 is electrically coupled to the shield wire 140 of the coaxial cable 110 via the epoxy 30. On the distal end of the silver epoxy 140 is an insulating substance, a non-conductive epoxy 35.

On the distal end of the non-conductive epoxy 35 is a layer of piezoelectric crystal ("PZT") 80, "sandwiched" between a conductive acoustic lens 70 and a conductive backing material 90, formed from an acoustically absorbent material (e.g., an epoxy substrate having tungsten particles). The acoustic lens 70 is electrically coupled with the center conductor wire 120 of the coaxial cable 110 via a connector 40 that is insulated from the silver epoxy 30 and the backing material 90 by the non-conductive epoxy 35. The backing material 90 is connected to the steel housing 20. It is desirable for the imaging transducer assembly 1 to be surrounded by a sonolucent media. Thus, the lumen 60 of the guidewire is also filled with saline around the assembly 1. The driveshaft 10, the housing 20, and the acoustic lens 70 are exposed to the saline. During operation, the PZT layer 80 is electrically excited by both the backing material 90 and the acoustic lens 70. The backing material 90 receives its charge from the shield wire 140 of the coaxial cable 10 via the silver epoxy 30 and the steel housing 30, and the acoustic lens 70, which may also be silver epoxy, receives its charge from the center conductor wire 120 of the coaxial cable 110 via the connector 40, which may be silver epoxy as well.

The imaging transducer assembly is generally a rigid structure; however, the vessels through which the assembly is typically advanced are often tortuous, which create tight radii within the catheter. Thus, it is desirable to have the rigid portions, such as the imaging transducer assembly, of the catheter be relatively small in length.

Accordingly, an alternative transducer assembly may be desirable.

SUMMARY OF THE INVENTION

The improved imaging device is intended for use within the lumen of a human body, e.g., the lumen of a blood vessel. Generally, the imaging device is coupled to the distal end of a drive shaft, and a conductive wire is wrapped around a distal portion of the drive shaft.

In one embodiment of the improved imaging device, the conductive wire is part of a sensor adapted to communicate with a medical positioning system.

In another embodiment of the improved imaging device, the conductive wire is configured to be a matching circuit for the imaging device.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

In order to better appreciate how the above-recited and other advantages and objects of the present inventions are obtained, a more particular description of the invention briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

FIG. 1a is a cross-sectional side view of an imaging transducer assembly known in the art;

FIG. 1b is a cross-sectional view of the coaxial cable within the prior art imaging transducer assembly of FIG. 1a;

FIG. 2a is cross-sectional side view of an imaging transducer assembly in accordance with an example embodiment of the invention;

FIG. 2b is a cross-sectional view of a coaxial cable within the imaging transducer assembly of FIG. 2a;

FIG. 3a is a simplified diagram of an electrical circuit formed by the imaging transducer assembly of FIG. 3a;

DETAILED DESCRIPTION OF THE PREFERRED EMBODIMENTS

Figures 1A, 1B:
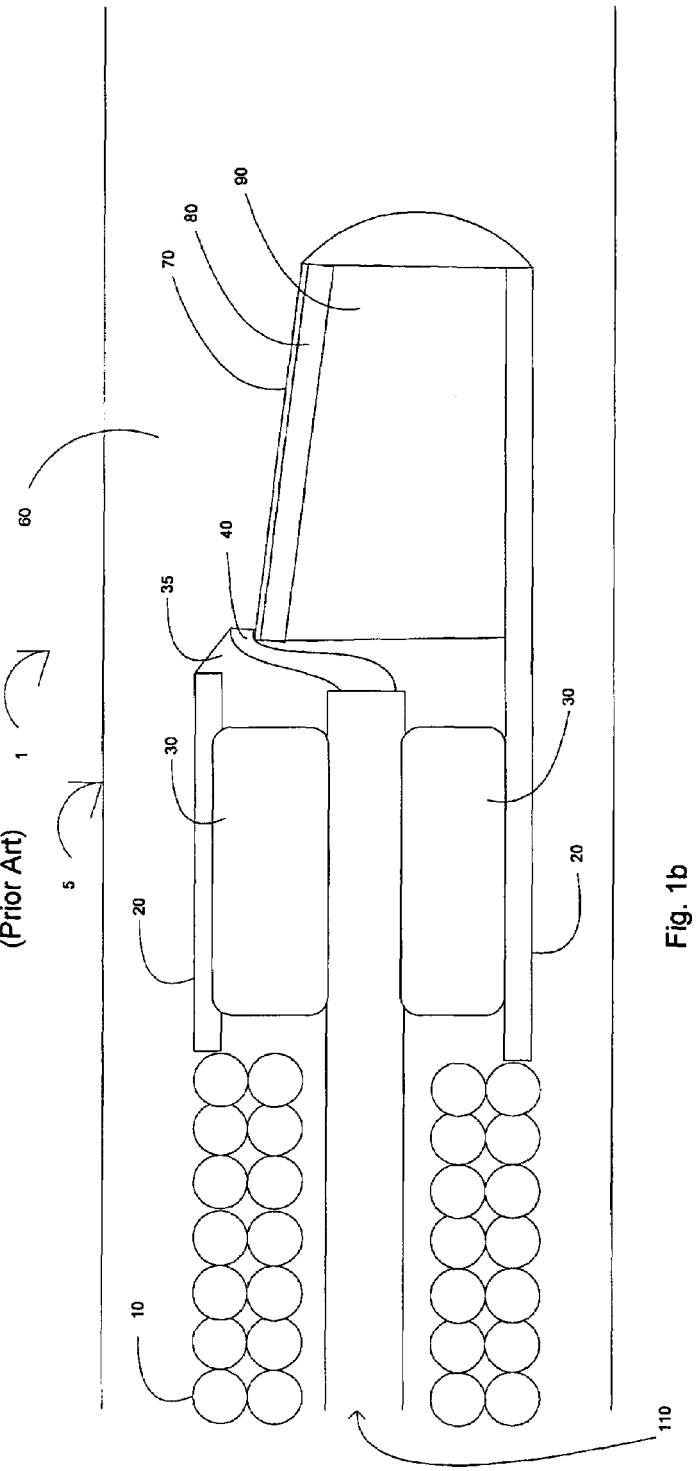

Described below is an improved imaging device assembly.

As mentioned above, an imaging device assembly is typically a rigid structure. However, because the assembly may travel through tortuous vessels, it may be preferable for the imaging device assembly to have a short length. In the particular embodiment described below, the imaging device assembly is an imaging transducer assembly. However, the invention may be adapted for use with other imaging devices instead.

One approach to reduce the length of the imaging transducer assembly is illustrated in FIG. 2a, which shows a cross-sectional side view of an imaging transducer assembly 300 in a lumen 305 of the distal portion of a guidewire or catheter assembly (partially shown) having an outer tubular wall 301. The imaging transducer assembly 300 includes a coaxial cable 410, having a center conductor wire 420, and an outer shield wire 430. The center conductor wire 420 is insulated from the outer shield wire 430, as shown in FIG. 2b, which shows a cross-section of the coaxial cable 410, where the shield wire 430 is surrounded by an insulating jacket 440. It should be noted that numerous alternative cable configurations may be used; for example, a cable having "twisted pair" wires may be used instead of a coaxial cable 410.

Turning back to FIG. 2a, surrounding the coaxial cable 410 is a layer of insulating material, such as a non-conductive epoxy 330. Surrounding the epoxy 330 is a drive shaft 310, which is a conductive wire wound around the epoxy 330/coaxial cable 410 to form a first coil shape. Preferably, the conductive wire is stainless and has a diameter of approximately 500 microns. Thus, the coaxial cable 410 is conductively insulated from the drive shaft 310.

The distal end of the imaging transducer assembly 300 includes an imaging device such as an imaging transducer 365. The imaging transducer 365 includes an electrically conductive backing material 390, having a top, bottom and center, which may be formed from an acoustically absorbent material (for example, an epoxy substrate having tungsten or silver particles). The center of the backing material 390 surrounds a shield pellet 400, which is electrically coupled to the shield wire 430 at the distal end of the coaxial cable 410. The top of the backing material 390 is coupled to the bottom of a layer of piezoelectric crystal (PZT) 380. The top of the PZT layer 380 is coupled to a conductive acoustic lens 370, which may include silver epoxy. The acoustic lens 370 is electrically coupled to the center conductor wire 420 of the coaxial cable 410 via a connector 360, which may include silver epoxy formed in the non-conductive epoxy 330 such that the connector 360 is insulated from the backing material 390.

The imaging transducer assembly 300 further includes an insulated conductive wire 325 tightly wound around the distal end of the drive shaft 310, forming a second coil shape. The wire 325 may be configured to be part of a sensor adapted to communicate with a medical positioning system (not shown), if desired. The wire 325 may transmit electromagnetic signals to be received by an external receiver, (e.g., active transmission) or the wire 325 may be otherwise detectable (e.g., passive) by an external device. The wire 325 may also have magnetic qualities. The two ends of the wire 325 are terminals that may receive an electric charge. One end 350 of the wire 325 is coupled to the connector 360 that electrically couples the acoustic lens 370 with the center conductor wire 420 of the coaxial cable 410. The other end of the wire 325 is coupled to the shield wire 430 of the coaxial cable 410 via a silver epoxy 340 coupled to the shield pellet 400.

The second coil shape 325 desirably provides an inductance if the wire 325 is configured to be part of a sensor to increase the sensor's ability to send and receive electromagnetic signals. Further, the second coil shape also serves as a housing to reinforce the imaging transducer assembly 300. This configuration relieves the need for a separate housing element, which may desirably reduce the length of the imaging transducer assembly 300, thus improving the ability of the catheter to pass through a tortuous pathway.

It should be noted that the conductive wire configuration 325 may have a variety of other shapes and configurations. For example, configuration 325 may be a solid structure instead of a coiled wire. The wire 325 is preferably copper and approximately 10 microns in diameter. The small diameter of the wire 325 allows the second coil shape to have a small impact on the dimensions of the imaging transducer assembly 300, thus allowing the imaging transducer assembly 300 to still work within the lumen 305 of the guidewire or catheter assembly.

To protect the wire 325 from abrasion damage, a polyester ("PET") shrink tube (not shown) may surround the imaging transducer assembly 300, covering the conductive wire 325. An opening is formed in the shrink tube where the acoustic beam is emitted from the imaging transducer 365. Shrink tubes made of PET are readily available in the commercial market with wall thickness below 0.0060 millimeters. Thus, the shrink tube adds little to the profile of the assembly 300. PET has a high tensile strength, as can be appreciated by one of ordinary skill in the art, and it has a dielectric strength to sufficiently insulate the electrical connections that could otherwise be exposed to the lumen 305.

Surrounding the coaxial cable 410 and the imaging transducer assembly 300, including the conductive wire 325, is non-conductive epoxy 330. The epoxy 330 electrically isolates the conductive wire 325 from the lumen 305, couples the imaging transducer assembly 300 to the driveshaft 310, reinforces the structure of the imaging transducer assembly 300, fills in gaps, and seals the perimeters of the shrink tube around the opening exposed for emission of the acoustic beam (not shown). The epoxy 330 may be a high strength epoxy that is curable via exposure to either ultra-violet ("UV") or ambient light of sufficient intensity. The epoxy 330 may also be curable via catatonic curing with a curing agent for shaded areas not accessible to light. The epoxy 330 may have medium viscosity to prevent excessive wicking into the driveshaft 310, which could undesirably increase the length of the imaging transducer assembly 300.

To facilitate the operation of the imaging transducer 365 of the imaging transducer assembly 300, the lumen 305 of the guidewire or catheter assembly is preferably filled with a sonolucent media, such as saline. If the conductive wire 325 is configured to be part of a sensor, then it may be desirable to have at least one of the ends 350, 340 of the wire 325 be insulated from the saline within the lumen 305 because if both ends, 350 and 340, were exposed to the saline, the semi-conductive nature of the saline might shunt the ends, 350 and 340, thus undesirably "shorting out" the sensor, and/or affecting the signal-to-noise ratio of the navigational signals. In light of this, the imaging transducer assembly 300 preferably has one end 340 of the wire 325 insulated from the drive shaft 310 and saline by the non-conductive epoxy 330. Further, because the wire 325 is insulated, the coil portion of the wire 325 is also insulated from the driveshaft 310 and the saline in the lumen 305. The other end 350 of the wire 325, however, may be exposed to the saline via the acoustic lens 370.

During the operation of the imaging transducer assembly 300, the PZT crystal 380 is electrically excited by both the backing material 390, charged through the shield wire 430, and the acoustic lens 370, charged through the center conductor wire 420. In addition, the conductive wire 325 is also charged by the shield wire 430 and the center conductor wire 420. If the conductive wire 325 is configured to send electromagnetic signals to nodes of a medical positioning system (not shown), then the charge may facilitate a broadcast, via the conductive wire 325. However, if the conductive wire 325 is configured to receive electromagnetic signals from one or more nodes of a medical positioning system (not shown), then separate circuitry including a signal processor may be used to filter and extract the desired electromagnetic signals. Other features and circuits may also be added as desired.

Figure 3A:
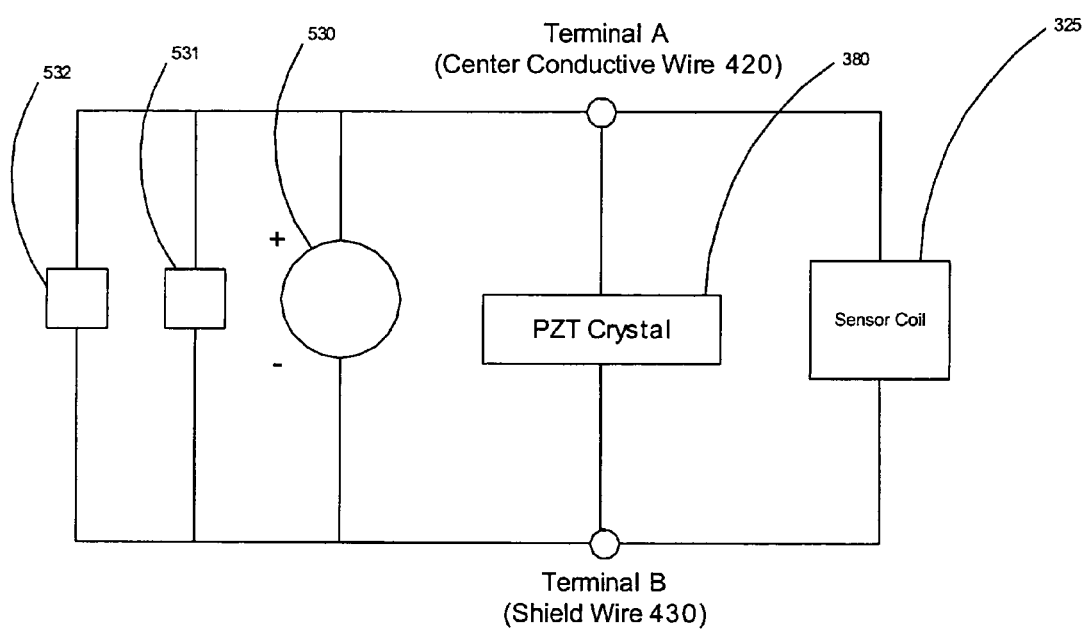

Thus, turning to FIG. 3a, the assembly 300 is depicted as a simplified electric circuit having an energy source 530, such as an ultrasound console, the load of the PZT layer 380, the load 325 of the sensor coil 225, which is in parallel with the load of the PZT layer 380, sensor circuitry 531, which may include a signal processor (not shown) to receive and process electromagnetic signals, i.e., navigational signals, from the sensor coil 325, as would be known to a person of skill in the art, transducer circuitry 532, which may also include a signal processor (not shown) to process imaging signals from the imaging transducer, and terminals A and B. Terminals A and B represent the center conductor wire 420 and the shield wire 430 of the coaxial cable 410, respectively. Other features and circuits may also be added as desired.

As can be appreciated by one of ordinary skill in the art, it may be desirable to couple the imaging transducer 365 with a matching circuit and/or tuning circuit ("matching/tuning circuit"). The matching/tuning circuit filters out undesirable reactance properties of the transducer 365 to optimize the transmitted beam energy emitted from the transducer 365, which may result in stronger echoes. In one embodiment of a transducer assembly 300, the conductive wire 325 may be utilized as a matching/tuning circuit in addition to, or alternatively to, a sensor adapted to communicate with a medical positioning system, wherein the sensor is configured to transmit electromagnetic signals. The wire 325 may be in parallel to the imaging transducer 365, as described above and shown in FIG. 3a, wherein the imaging transducer 365 is represented as just the PZT crystal 380.

Figure 3B:
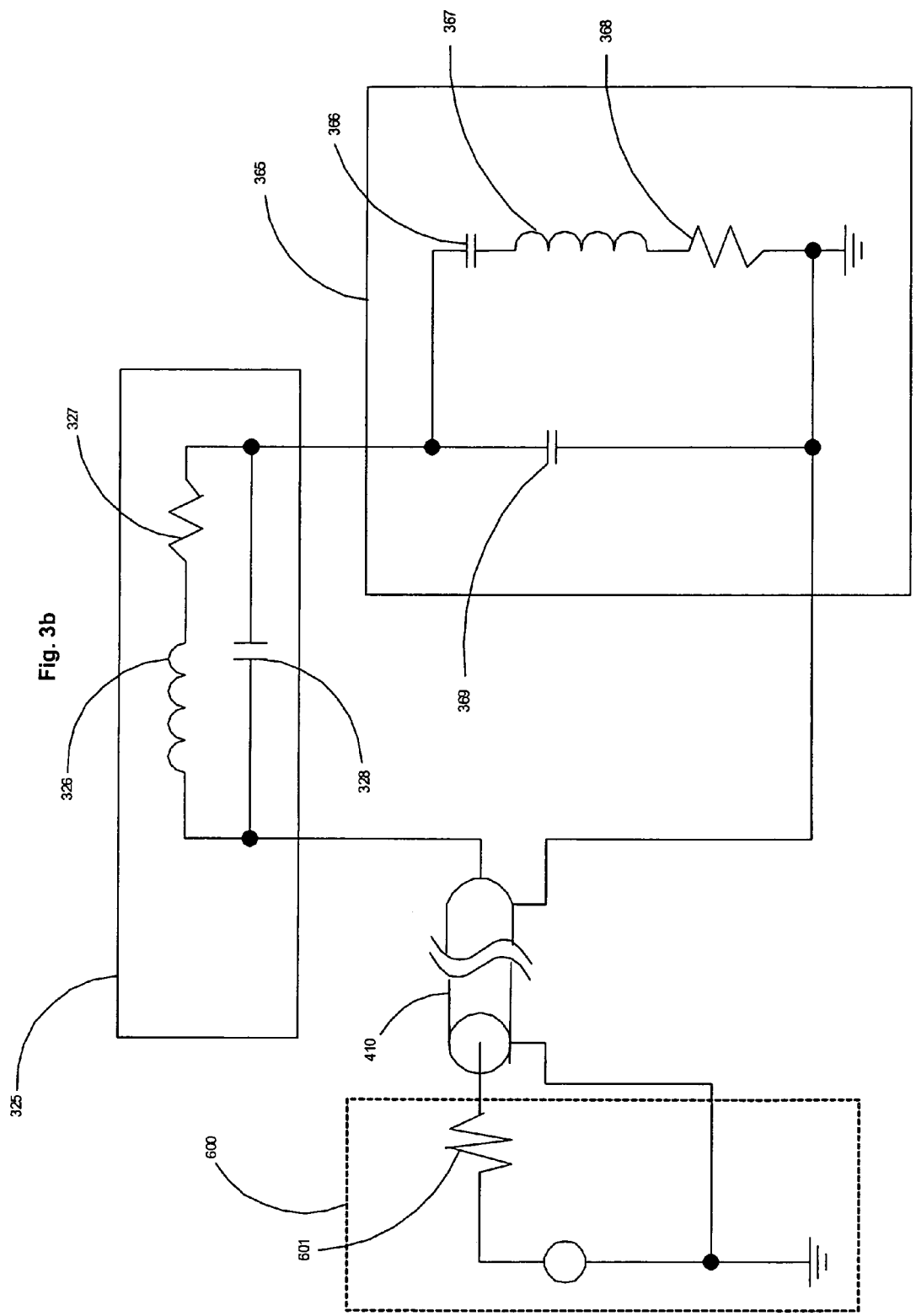
FIG. 3b is a simplified diagram of an alternative electrical circuit formed an imaging transducer assembly in accordance with an example embodiment of the invention.

Alternatively, the transducer 365 may be configured to be in series with the wire 325, as shown in FIG. 3b. The imaging transducer 365 may be represented as a first capacitor 366, inductor 367, and resistor 368 coupled together in series and a second capacitor 369, coupled in parallel to the first capacitor 366, inductor 367, and resistor 368. The second capacitor 369 represents the undesirable reactance of the transducer 365. In one example, the first capacitor 366 may have a value of 8.78 pf, the inductor 367 may have a value of 2.05 uH, the resistor 368 may have a value of 175 ohms, and the second capacitor 369 may have a value of 28.4 pf.

Inductors are often used in matching/tuning circuits to filter, or tune out, the reactance of the parallel capacitance of the transducer 365, i.e., second capacitor 369. For the above example, it may be desirable to have an inductor be configured to have an inductance of approximately 470 uH in series with the transducer 365, as shown in FIG. 3b. The conductive wire 325 may be configured to have the desired inductance. In FIG. 3b, the conductive wire 325 is represented as an inductor 326 in series with a resistor 327, and a capacitor 328 in parallel with the inductor 326 and resistor 327. In one example, the inductor 326 has a value of 470 uH, the resistor has a value of 50 ohms, and the parallel capacitor 328 has a value of 5 nf. An energy source 600, such as an ultrasound console, having a resistive component 601, is coupled to the transducer 365 and the conductive wire 325 via the coaxial cable 410. In the example above, the resistive component 601 may have a value of 50 ohms.

If the energy source is an ultrasound console, then the conductive wire 325, set up as a matching/tuning circuit and a sensor, may be configured such that it resonates at or near the same frequency as the imaging transducer 365, which provides tuning for the transducer 365. The pulse generated by the ultrasound console may provide excitation to both the transducer 365 and the wire 325. If tuning/matching are not desired, then the wire 325 may be configured to resonate at a different frequency, preferably within the imaging period of the transducer 365. Accordingly, a narrower pulse from the ultrasound console may excite the transducer 365 only, then a longer pulse, which will excite the conductive wire 325 only, may follow the narrower pulse. The length of the longer pulse may be determined by the desired resonant frequency of the conductive wire 325 and the transducer 365. Thus, if the conductive wire 325 is configured to be a sensor of a medical positioning system, multiple receivers (not shown), adapted to receive signals from the sensor, may be coupled with the ultrasound console whereby the ultrasound console will process information from the receivers and provide the coordinates of the wire 325.

Figure 3C:
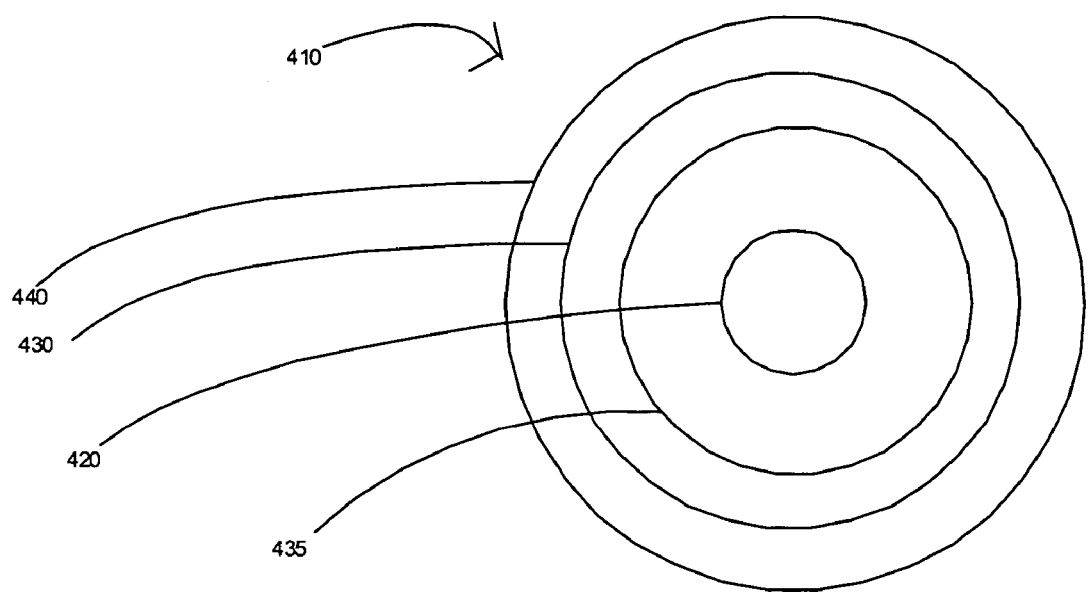
FIG. 3c is a cross-sectional view of a tri-axial cable within an imaging transducer assembly in accordance with an example embodiment of the invention.

If the conductive wire 325 is used as both a matching/tuning circuit and a sensor, then the matching/tuning aspect of the wire 325 may overly influence the sensor aspect. One approach to alleviate this is to use a tri-axial cable, as shown in FIG. 3c. A tri-axial cable may include a center conductor wire 420, an outer shield wire 430, and a middle wire 435. Each of the wires 420, 430, and 435 are insulated from each other. In addition, the outer shield wire 430 is surrounded by an insulating jacket 440. By using the tri-axial cable, the conductive wire 325 may be electrically coupled with a separate matching/tuning circuit, wherein the matching/tuning circuit and the conductive wire 325 each have separate electrical paths. With this configuration, the matching/tuning circuit may not overly influence the sensor. The matching/tuning circuit may include a "T" network, a "pi" network, a series or parallel inductance, or a transformer. It should be noted that numerous alternative cable configurations may be used; for example, a cable having a "twisted" configuration may be used instead of an "axial" configuration.

Figure 4:
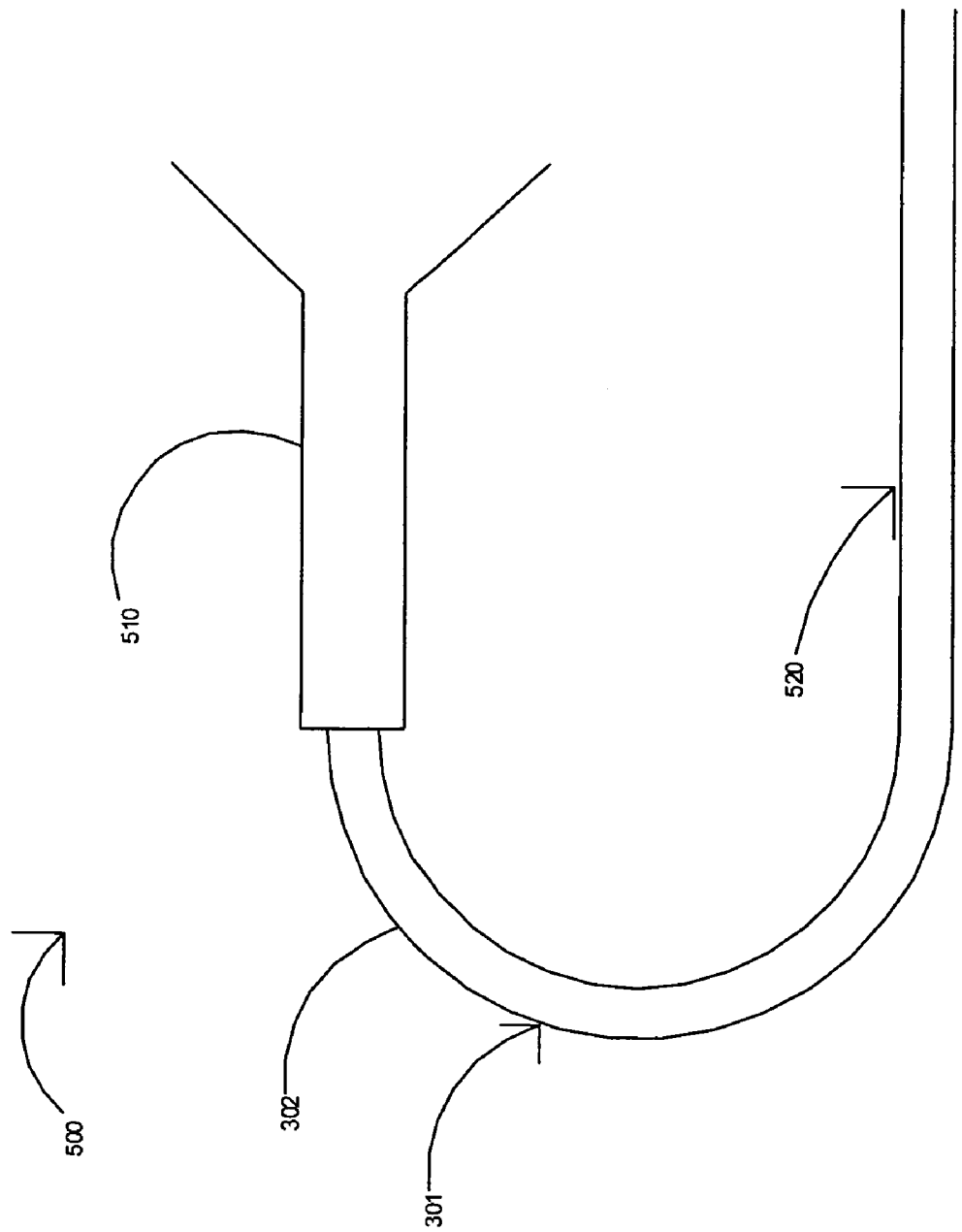
FIG. 4 is a partial cross-sectional side view of a catheter in accordance with an example embodiment of the invention.

Turning to FIG. 4, the transducer/sensor assembly 300 may be placed in a distal portion 520 of a guidewire 500. The guidewire 500 may comprise a guidewire body 302 in the form of a flexible, elongate tubular member, having an outer wall 301. The guidewire body 302 may be formed of any material known in the art including nitinol hypotube, metal alloys, composite materials, plastics, braided polyimide, polyethylene, peek braids, stainless steel, or other superelastic materials.

The length of the guidewire 500 may vary depending on the application. In a preferred embodiment, the length of the guidewire 500 is between 30 cm and 300 cm. A catheter (not shown) may be configured to use several different diameters of guidewires 500. For example, the guidewire 500 may have a diameter of 0.010, 0.014, 0.018, or 0.035 inches. Typically, the diameter of the guidewire 500 is uniform.

A proximal portion 510 of the guidewire 500 may be adapted to connect to circuitry (not shown) that processes imaging signals from the imaging transducer and/or circuitry (not shown) that processes navigational signals from the sensor 320., such circuits being well known.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention can be performed using different or additional process actions, or a different combination or ordering of process actions. For example, this invention is particularly suited for applications involving medical imaging devices, but can be used on any design involving imaging devices in general. As a further example, each feature of one embodiment can be mixed and matched with other features shown in other embodiments. Additionally and obviously, features may be added or subtracted as desired. Accordingly, the invention is not to be restricted except in light of the attached claims and their equivalents.

What is claimed is:

1. An imaging apparatus for use within the lumen of a blood vessel comprising:
    a catheter having a lumen, said catheter comprising, within the lumen:
        a non-conductive epoxy layer surrounding a cable;
        a drive shaft, having distal and proximal ends, surrounding a substantial portion of the non-conductive epoxy layer;
        an imaging device coupled to the distal end of the drive shaft; and
        a sensor coil wound around a distal portion of the drive shaft, wherein the sensor coil is configured to communicate with a medical positioning system by transmitting or receiving electromagnetic signals to or from the medical positioning system and is electrically isolated from the lumen of the catheter.

2. The imaging apparatus of claim 1, wherein the sensor coil is electrically coupled to the imaging device in parallel.

3. The imaging apparatus of claim 1, wherein the sensor coil is electrically coupled to the imaging transducer in series.

4. The imaging apparatus of claim 1, further comprising a coaxial cable, surrounded by the non-conductive epoxy.

5. The imaging apparatus of claim 1, further comprising a tri-axial cable, surrounded by the non-conductive epoxy.

6. The imaging apparatus of claim 1, wherein the imaging device is an imaging transducer.

7. The imaging apparatus of claim 6, wherein the imaging transducer assembly comprises an acoustic lens coupled with a piezoelectric crystal layer, and the piezoelectric crystal layer is coupled with a backing material.

8. The imaging apparatus of claim 7, wherein the backing material comprises tungsten.

9. The imaging apparatus of claim 1, further comprising a shrink tube surrounding the imaging device and the sensor coil.

10. The imaging apparatus of claim 1, wherein the sensor coil is adapted to communicate with a medical positioning system.

11. The imaging apparatus of claim 10, wherein the sensor coil is configured to transmit electro-magnetic signals.

12. The imaging apparatus of claim 10, wherein the sensor coil is configured to receive electro-magnetic signals.

13. An imaging apparatus for use within the lumen of a blood vessel comprising:
    a catheter having a lumen, said catheter comprising, within the lumen:
        a non-conductive epoxy layer surrounding a cable;
        a drive shaft, having distal and proximal ends, surrounding a substantial portion of the non-conductive epoxy layer;
        an imaging device coupled to the distal end of the drive shaft; and
        a sensor coil coupled to a distal portion of the drive shaft, wherein the sensor coil is configured to communicate with a medical positioning system by transmitting or receiving electromagnetic signals to or from the medical positioning system and is electrically isolated from the lumen of the catheter, and wherein the sensor coil is configured to be a tuning circuit for the imaging transducer.

14. An imaging apparatus for use within the lumen of a blood vessel comprising:
    a catheter having a lumen, said catheter comprising, within the lumen:
        a non-conductive epoxy layer surrounding a cable;
        a drive shaft, having distal and proximal ends, surrounding a substantial portion of the non-conductive epoxy layer;
        an imaging device coupled to the distal end of the drive shaft;
        a sensor coil coupled to a distal portion of the drive shaft, wherein the sensor coil is configured to communicate with a medical positioning system by transmitting or receiving electromagnetic signals to or from the medical positioning system and is electrically isolated from the lumen of the catheter; and
        a matching circuit coupled with the sensor coil.

15. The imaging apparatus of claim 14, wherein the matching circuit comprises a pi network.

16. A medical imaging system comprising:
    a medical positioning system; and
    an imaging device adapted to be inserted into a lumen of a body, the imaging device including:
    a catheter having distal and proximal ends and a lumen;
    a drive shaft, having proximal and distal ends, within the lumen; and
    an imaging transducer assembly, including:
        an imaging transducer coupled to the distal end of the drive shaft; and
        a coil of a sensor wound around a distal portion of the drive shaft, the sensor adapted to communicate with the medical positioning system, wherein the sensor is electrically isolated from the lumen of the catheter.

17. The medical imaging system of claim 16, wherein the imaging transducer comprises an acoustic lens coupled with a layer of piezoelectric crystal, the piezoelectric crystal being coupled with a backing material.

18. The medical imaging system of claim 16, wherein the medical positioning system includes an ultrasound console that sends pulses to the coil and the imaging transducer.

19. The medical imaging system of claim 16, wherein the coil is electrically coupled to the transducer in series.

20. The medical imaging system of claim 16, wherein the coil is electrically coupled to the transducer in parallel.

21. The medical imaging system of claim 16, further comprising a coaxial cable surrounded by the drive shaft.

22. The medical imaging system of claim 16, further comprising a tri-axial cable surrounded by the drive shaft.

23. The medical imaging system of claim 16, further comprising a non-conductive epoxy layer surrounding the coil of the sensor.

24. The medical imaging system of claim 23, wherein the non-conductive epoxy layer surrounds the imaging transducer and couples the imaging transducer to the distal end of the drive shaft.

25. A medical imaging system comprising:
a medical positioning system; and
an imaging device adapted to be inserted into a lumen of a body, the imaging device including:
a catheter having distal and proximal ends and a lumen;
a drive shaft, having proximal and distal ends, within the lumen; and
an imaging transducer assembly, including:
an imaging transducer coupled to the distal end of the drive shaft;
a coil of a sensor at a distal portion of the drive shaft, the sensor adapted to communicate with the medical positioning system, wherein the sensor is electrically isolated from the lumen of the catheter; and
a matching circuit coupled with the imaging transducer.

26. The medical imaging system of claim 25, wherein the coil is configured to be the matching circuit.

* * * * *